United States Patent [19]
Manzie et al.

[11] Patent Number: 5,505,707
[45] Date of Patent: Apr. 9, 1996

[54] TUBING SYSTEM WITH PUMP FOR DELIVERING CONTINUOUS FLUID FLOW OR FLUID BOLUS TO A SURGICAL SITE

[75] Inventors: Peter Manzie, Berwyn; Albert Nowosielski, Roselle, both of Ill.

[73] Assignee: Northgate Technologies, Inc., Elgin, Ill.

[21] Appl. No.: 348,544

[22] Filed: Dec. 1, 1994

[51] Int. Cl.⁶ ................................................. A61M 37/00
[52] U.S. Cl. ........................... 604/131; 604/142; 604/247
[58] Field of Search ..................... 604/142, 141, 604/80, 131, 133, 246, 253, 251, 247, 257, 83, 81, 82

[56] References Cited

U.S. PATENT DOCUMENTS

| | | | |
|---|---|---|---|
| 3,900,022 | 8/1975 | Widran | 128/7 |
| 4,180,074 | 12/1979 | Murry et al. | 128/276 |
| 4,391,599 | 7/1983 | Jenkins | 604/118 |
| 4,432,754 | 2/1984 | Urqhart et al. | 604/80 X |
| 4,439,179 | 3/1984 | Lueders et al. | 604/34 |
| 4,573,974 | 3/1986 | Ruschke | 604/81 |
| 4,604,089 | 8/1986 | Santangelo et al. | 604/30 |
| 4,613,325 | 9/1986 | Abrams | 604/65 |
| 4,650,462 | 3/1987 | DeSatnick et al. | 604/30 |
| 4,655,197 | 4/1987 | Atkinson | 128/66 |
| 4,702,733 | 10/1987 | Wright et al. | 604/34 |
| 4,713,051 | 12/1987 | Steppe et al. | 604/30 |
| 4,820,265 | 4/1989 | DeSatnick et al. | 604/30 |
| 4,874,359 | 10/1989 | White et al. | 604/4 |
| 4,940,457 | 7/1990 | Olson | 604/30 |
| 5,004,459 | 4/1991 | Peabody et al. | 604/29 |
| 5,019,038 | 5/1991 | Linden | 604/49 |
| 5,053,002 | 10/1991 | Barlow | 604/30 |
| 5,059,182 | 10/1991 | Laing | 604/142 |
| 5,061,241 | 10/1991 | Stephens, Jr. et al. | 604/114 |
| 5,098,387 | 3/1992 | Wiest et al. | 604/153 |
| 5,152,746 | 10/1992 | Atkinson et al. | 604/31 |
| 5,356,379 | 10/1994 | Vaillancourt | 604/131 X |

FOREIGN PATENT DOCUMENTS

| | | | |
|---|---|---|---|
| 2371202 | 7/1978 | France | A61M 1/03 |

*Primary Examiner*—John D. Yasko
*Attorney, Agent, or Firm*—Willian Brinks Hofer Gilson & Lione

[57] ABSTRACT

A tubing set for connecting a source of irrigating fluid to an intraoperative surgical instrument having a fluid delivery passage therein. The tubing set includes a first section having an inlet for connection to the source of irrigating fluid, a second section having an outlet for connection to the intraoperative medical instrument, and a pump connected between the first section and the second section. A valve is located between the inlet and the outlet and restricts flow so that flow is in a direction from the inlet toward the outlet. The tubing set can deliver a continuous flow or trickle of fluid from the source of irrigating fluid to the medical instrument and can deliver a bolus of fluid to the surgical instrument upon operation of the pump.

31 Claims, 5 Drawing Sheets

TUBING SYSTEM WITH PUMP FOR DELIVERING CONTINUOUS FLUID FLOW OR FLUID BOLUS TO A SURGICAL SITE

BACKGROUND OF THE INVENTION

The present invention relates to a system for providing fluid to a site inside the body and in particular the present invention relates to an irrigation tubing set system and method for providing fluid flow continuously or for delivering a bolus of fluid for irrigating or flushing an internal body site or organ that is accessed through a relatively small incision, natural orifice of the body, or in conjunction with a laparoscope, endoscope, resectoscope or similar device.

Certain medical procedures, such as cystoscopy and ureteroscopy, as well as other urological, gynecological, and laparoscopic procedures and surgeries, are performed inside the body through an apparatus, through a very small incision, or through a small natural orifice of the body. Instruments used to perform these types of surgical procedures include resectoscopes, irrigation-aspiration cannula, laparoscopes, and so on. In addition, certain medical diagnostic procedures are performed by accessing an internal body site through a small incision or natural orifice and inserting an endoscope to enable the physician to view the internal body site.

When performing these types of surgeries or diagnostic procedures, it is sometimes necessary for the physician to apply small volumes of a fluid, such as water, to flush blood or tissue from the surgical area to enable the procedure to proceed. Some surgical instruments and endoscopes, especially those used for urological procedures, are provided with flow channels to allow the physician to apply a flushing or irrigating fluid to the internal body site or to expand a body cavity. This is typically done by suspending one or more plastic bags containing the irrigating fluid on an IV pole and connecting the bags to the inlet of the flow channel of the surgical instrument with conventional plastic tubing. To control flow from the bags to the instrument, a clamp may be positioned on the tubing. If the physician desires to flush the site with water, he can loosen the clamp. Although this arrangement may be suitable for some procedures, it has some limitations. For example, it may be difficult to control the fluid pressure being applied by the suspended bags to the instrument. In addition, it may be inconvenient or awkward for the physician to adjust the clamp to control the flow while also handling the surgical instrument. In addition, the volume and pressure of water being delivered may be difficult to control.

Accordingly, it is an object of the present invention to provide a system and method that addresses or overcomes the disadvantages of the prior methods of fluid delivery to an internal body site. Such a system may also find application in other medical and non-medical fluid delivery systems.

SUMMARY OF THE INVENTION

To address the above concerns, the present invention provides a tubing set for connecting a source of irrigating fluid to an intraoperative surgical instrument having a fluid delivery passage therein. The tubing set includes a first section having an inlet for connection to the source of fluid, a second section having an outlet for connection to the medical instrument, and a pump connected between the first section and the second section. A valve is located between the inlet and the outlet and restricts flow in a direction from the source to the surgical instrument. The tubing set can be operated to deliver a continuous, relatively unrestricted flow of fluid from the source of irrigating fluid to the surgical instrument or can be operated to deliver a smaller continuous flow, such as a trickle, by appropriate adjustment. Further, the tubing set can be used to deliver a bolus of fluid to the surgical instrument upon operation of the pump.

DESCRIPTION OF THE PREFERRED EMBODIMENTS

Figure 1:
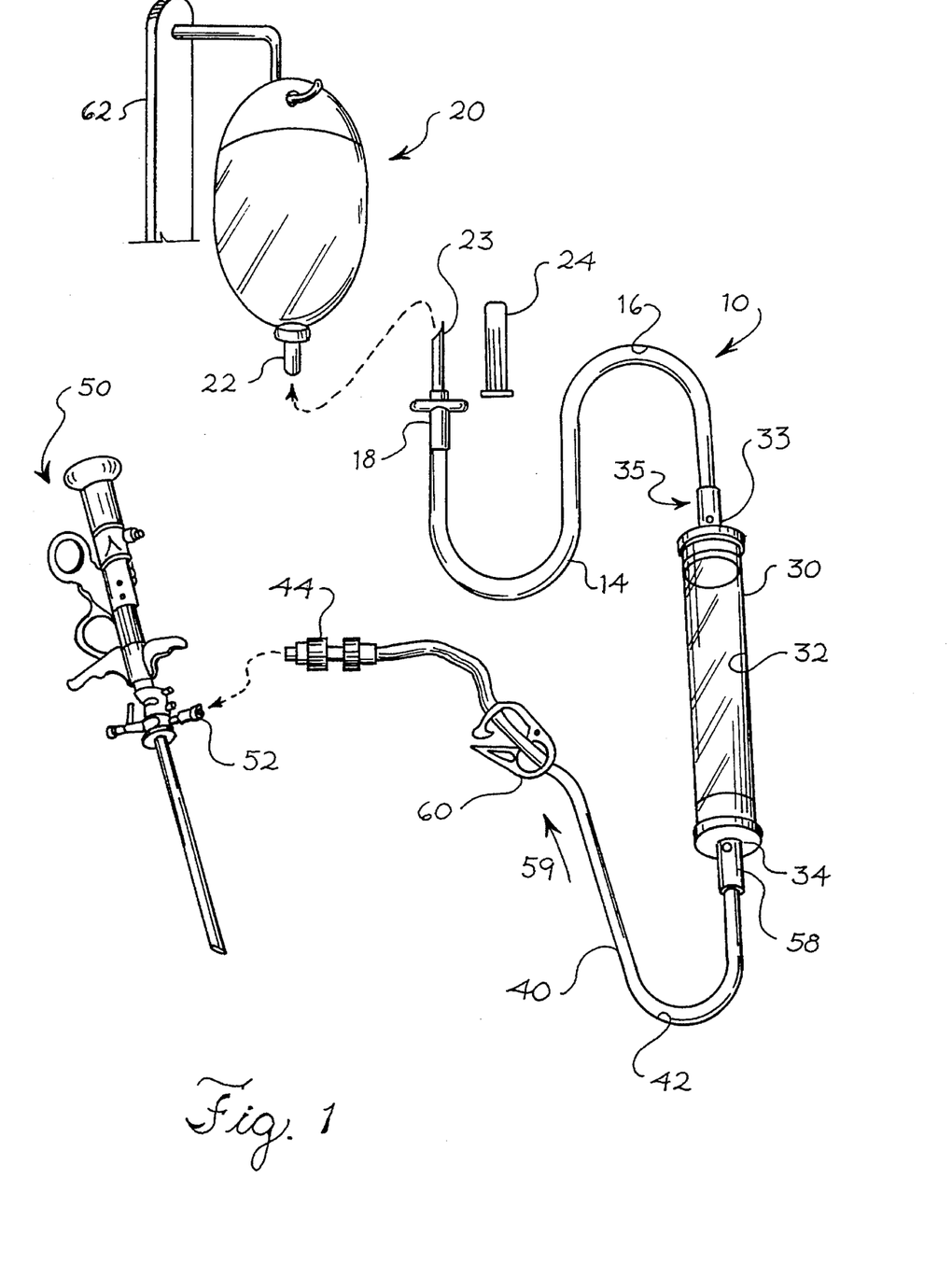
FIG. 1 is a perspective view of a first embodiment of the present invention, shown in relation to a source of irrigating fluid and a surgical instrument.

Referring to FIG. 1 there is shown a first preferred embodiment of the present invention. The embodiment shown in FIG. 1 is a tubing set or system 10 that is used to provide a liquid, such as sterile water or saline, to an intraoperative instrument. The intraoperative instrument may be used in conjunction with a procedure that accesses an internal body site through a small surgical incision or natural orifice. These procedures may be for diagnostic or therapeutic purposes and include in particular cystoscopy and ureteroscopy, as well as other urological, transurethral, gynecological and laparoscopic diagnostic procedures and surgeries.

The tubing system 10 includes a first section of tubing 14 that defines a first fluid passage 16. The first section of tubing 14 is preferably composed of polyvinylchloride (PVC) tubing with an I.D. of approximately 0.20 inches and a length of approximately 8 feet, although other sizes and materials may also be suitable. Located at one end of the tubing 14 is a fitting 18 that provides a fluid inlet to the fluid passage 16 defined by the first section of tubing 14. The fitting 18 provides for a suitable connection with a source of irrigating fluid 20. According to the first embodiment, the source of irrigating fluid is comprised of one or more conventional bags of saline water, although alternatively the source of fluid may be other fluids used in conjunction with medical procedures for irrigation of surgical sites. The source of fluid 20 typically has a fitting 22 located thereon. The fitting 18 on the tubing 14 is suitable for making a matable connection with the fitting 22 on the bag 20. In one embodiment, the fitting 18 on the tubing 14 may be a spike 23 suitable for piercing a membrane in the fitting 22 of the bag 20. A spike cover 24 may be provided to enclose the spike 23 during shipment, storage, and handling of the tubing set 10 and is removed by the physician prior to use of the tubing. Other types of matable fittings or adapters are also considered to be suitable. For example, the fitting 18 on the tubing 14 may be a luer lock-type fitting, that is matable with a corresponding type of fitting 22 on the bag 20.

Connected to the opposite end of the first section of tubing 14 is a pump 30. In this embodiment, the pump 30 is a tubular pump composed of a resilient, hollow, flexible plastic tube defining an internal chamber or volume 32 having an inlet 33 and an outlet 34. The internal chamber 32 of the pump 30 is in fluid communication with the first fluid passage 16 via the inlet 33. In this embodiment, the pump 30 fills with fluid under pressure applied by the source of fluid 20. In the first embodiment, the tubular pump is appropriately sized for grasping manually. Accordingly, the tubular pump is approximately 4¾ inches in length and ⅞ inches in diameter. The tubular pump is preferably made of PVC. A suitable tubular pump is commercially available from Miles, Covina Calif.

Located in the first fluid flow passage 16 between the source of fluid 20 and the pump 30 is a first valve 35. The first valve 35 may be a one-way or check valve and is oriented so that it restricts flow in the first fluid flow passage 16 so that fluid flow is in the direction from the source of fluid 20 toward the pump 30 and not from the pump 30 back toward the source of fluid 20. In the first embodiment, a commercially available check valve may be used, such as a plastic or metal ball-type valve available from Miles, Covina, Calif. In the first embodiment, the first valve 35 is inserted in line with the first tubing section 14 between the distal end of the tubing 14 and the inlet 33 to the pump 30. Alternatively, the first tubing section 14 may be formed of two parts with the first valve 35 located between the two parts.

Connected to the outlet 34 of the tubular pump 30 is a second section of tubing 40. The second section of tubing 40 defines a second fluid passage 42. The second section of tubing may also be composed of PVC tubing with an I.D. of approximately 0.20 inches. The second section of tubing 40 has a length of approximately 2 feet, although other sizes and materials may also be suitable. Located at a distal end of the second section of tubing 40 is a second fitting 44 that provides for a fluid outlet from the second fluid passage 42. The second fitting 44 provides for a suitable connection with an intraoperative instrument 50 which may be a cystoscope. The intraoperative instrument 50 has a fitting 52 located thereon. The fitting 44 at the end of the second section of tubing 40 is preferably suitable for making a matable connection with the fitting 52 on the intraoperative instrument 50. In one embodiment, the fitting 44 on the second section of tubing 40 is a rotating male luer lock-type fitting and the fitting 52 on the intraoperative instrument 50 is a female luer lock-type fitting. Other types of matable fittings or adapters may also be used.

Located in the second fluid flow passage 42 between the pump 30 and the intraoperative instrument 50 is a second valve 58. The second valve 58 may be a one-way or check valve and is oriented so that it restricts flow in the second fluid flow passage 42 so that fluid flow is in the direction from the pump 30 toward the intraoperative instrument 50 (direction of arrow 59) and not from the intraoperative instrument 50 back toward the pump 30. In the first embodiment, a commercially available check valve may be used, such as a plastic or metal ball-type available from Miles, Covina, Calif. In the first embodiment the second valve 58 is inserted in line with the second tubing section 40 between the distal outlet 34 of the pump 30 and the proximal inlet to the second tubing section 40. Alternatively, the second tubing section 40 may be formed of two parts with the valve 58 located between the two parts.

In addition, a tubing clamp 60 is provided on the second section of tubing 40. The tubing clamp 60 may be of a conventional type that is located on the exterior of the flexible second section of tubing 40 and is manually operable to releasibly squeeze the exterior of the second section of tubing 40 to restrict the flow therethrough. The clamp 60 is preferably of the type that provides for a range of adjustment positions from fully open to fully closed.

To use the irrigation tubing set 10 of FIG. 1 in an intraoperative procedure, the fitting 18 of the irrigation tubing set 10 is connected to the source of fluid 20, as shown. The source of fluid 20 is preferably provided by suspending one or more bags of water on an IV pole 62 so that the fluid flows by gravity through the tubing set 10. The tubing set 10 is preferably primed by actuating the pump 30 repeatedly to expel substantially all air from the tubing set. Then, the irrigation tubing set 10 is connected to the intraoperative instrument 50. The clamp 60 is opened so that fluid flows through the intraoperative instrument 50. The delivered fluid pressure is provided by the height of the water bag above the intraoperative instrument 50. In this way, the fluid pressure is relatively low, relatively constant and easily controlled. Because the valve 58 permits fluid flow from the fluid source 20 toward the intraoperative instrument 50, fluid will flow through the continuous fluid path provided by the first section of tubing 14, the pump 30, and the second section of tubing 40. This rate of fluid flow is a function of the fluid pressure (i.e. which is related to the height of the fluid source bag) and the resistance of the entire fluid path. The resistance of the fluid path may be adjusted by manual adjustment of the clamp 60. If the clamp 60 is fully open, fluid will flow freely through the tubing set 10 and the fluid flow can be relatively high. The clamp 60 may be adjusted to restrict the flow through the tubing set 10 so that the flow rate is relatively low, e.g. a trickle. The flow rate may also be adjusted by changing the height of the hanging bags 20. Thus, the irrigation tubing set 10 may provide for a continuous flow or trickle of fluid from the fluid source 20 to the intraoperative instrument 50. This continuous flow or trickle is advantageous as it helps to irrigate the surgical site and keeps the surgical area around the tip of the intraoperative instrument clear. Also, the trickle flow is low enough so that it does not interfere with normal progress of the surgical procedure.

The irrigation tubing set 10 of FIG. 1 has the further advantage that it can be used to provide a relatively large amount of water, if desired. Although a small flow or trickle of water may be desirable on a continuous basis, occasionally the physician may need to deliver a substantial amount of water to flush an area. In order to provide a relatively large amount (i.e. a bolus) of water to the surgical site, the physician can operate the pump 30. This is readily performed in the embodiment of FIG. 1 by manually squeezing the tubular pump 30. As mentioned above, the pump 30 becomes filled with water when the irrigation tubing set is connected to the source of fluid 20. Upon squeezing the tubular pump, the fluid pressure inside the pump increases. Therefore, the fluid is delivered through the second section of tubing 40 toward the intraoperative instrument 50 and to the surgical site. The first valve 35 prevents fluid from flowing from the pump 30 back into the fluid source 20 when the pump 30 is squeezed. The second valve 58 allows fluid to flow from the pump 30 toward the intraoperative instrument, but prevents fluid from being back pressured toward the fluid source, especially if the bag of water runs out.

The embodiment of FIG. 1 may be used in conjunction with surgeries in which the operative site is not pressurized (i.e. at ambient pressure). In addition, the embodiment of FIG. 1 could also be used in conjunction with surgical procedures in which the operative site is pressurized (e.g. insufflated) provided that the relative pressures were taken into account. Also, although the pump of FIG. 1 is described as a tubular pump, other types of pumps may also be used such as bulb pumps, syringes, foot pedal type pumps, piston pumps, and so on.

Figure 2:
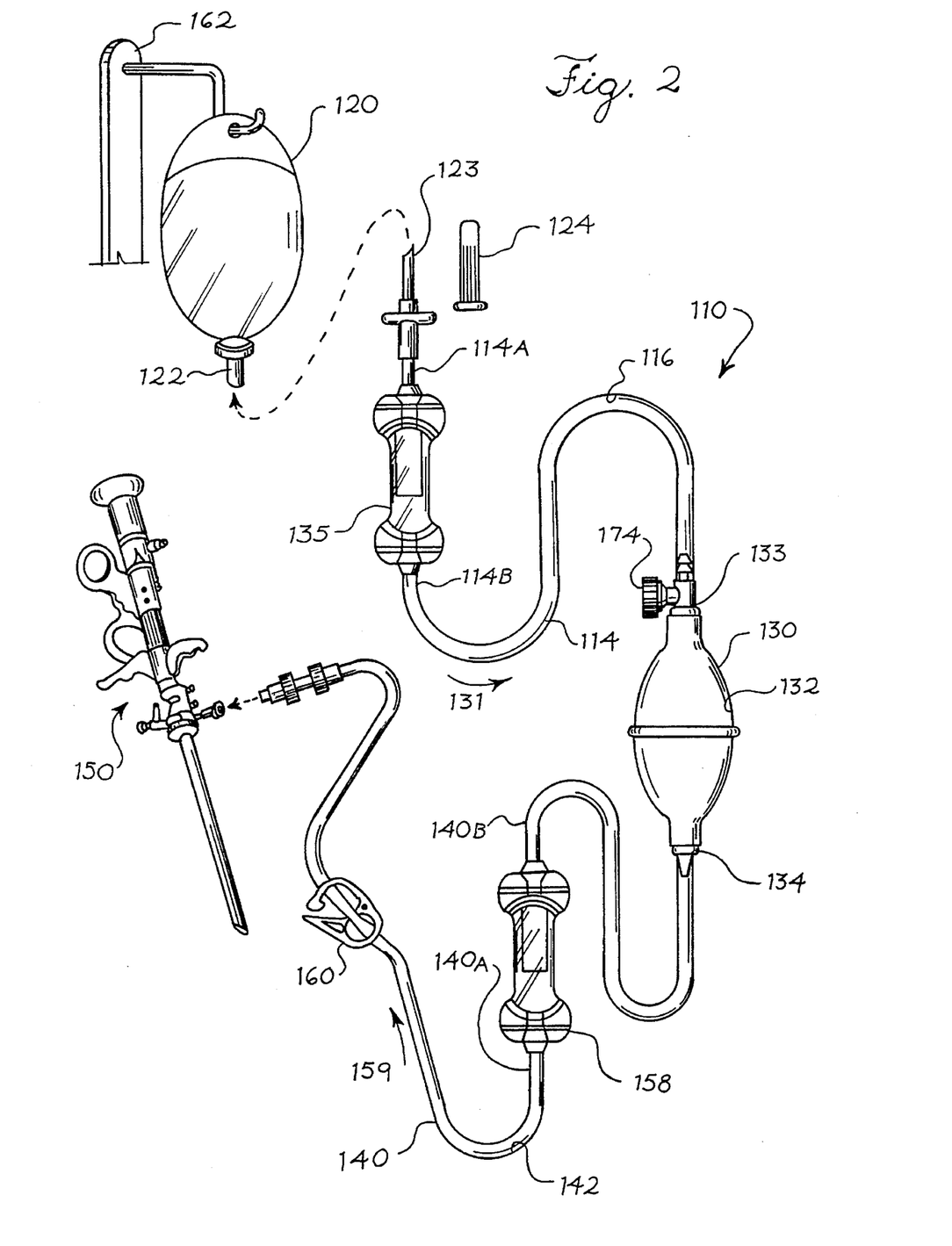
FIG. 2 is a perspective view similar to that of FIG. 1 showing another embodiment of the present invention.

Referring to FIG. 2, there is shown a second embodiment of the present invention. The second embodiment is similar in certain respects to the first embodiment and similar components are indicated by the same numerals incremented by 100. Components in the second embodiment may have the same size and composition as similar components in the first embodiment, except where noted.

In the embodiment of FIG. 2, there is an irrigation tubing set 110 having a first section of tubing 114 that defines a first fluid passage 116. A fitting 118, such as a spike 123, provides for a suitable connection with a fitting 122 on a source of irrigating fluid 120. As in the first embodiment, a spike cover 124 may be provided.

Connected to the opposite end of the first section of tubing 114 is a pump 130. In this embodiment, the pump 130 is a bulb pump. The bulb pump is composed of a resilient, hollow, flexible plastic bulb defining an internal chamber 132 and having an inlet 133 and an outlet 134. The internal chamber 132 is in fluid communication with the first fluid passage 116. The bulb pump 130 fills with fluid and assumes an expanded size under pressure applied by the source of fluid 120. The bulb pump is sized appropriately for grasping manually. For example, the bulb pump is approximately 4 inches in length and 1⅝ inches in diameter. A suitable bulb pump is commercially available from Halkey-Roberts Corp. of St. Petersburg, Fla.

Connected to the outlet 134 of the pump 130 is a second section of tubing 140 defining a second fluid passage 142. Located at a distal end of the second section of tubing 140 is a second fitting 144 that provides for a suitable connection with a fitting 152 on an intraoperative instrument 150. A tubing clamp 160 is located on the second section 140 of tubing.

Located in the first fluid flow passage 116 between the source of fluid 120 and the pump 130 is a first valve 135. The first valve 135 is oriented so that it restricts flow in the first fluid flow passage 116 so that fluid flow is in the direction from the source of fluid 120 toward the pump 130 (direction of arrow 131) and not from the pump 130 back toward the source of fluid 120. A commercially available valve may be used, such as a welded pillow valve available from Haemotronic, Fairfield, N.J. In this embodiment, the first tubing section 114 is formed of two parts, 114A and 114B, with the first valve 135 located between the two parts.

The second embodiment 110 also includes a second valve 158 located in the second fluid flow passage 142 to restrict flow in the direction from the pump 130 toward the intraoperative instrument 150 (direction of arrow 159). In this embodiment, the second valve 158 may be identical to the first valve 135. In this embodiment, the second tubing section 140 is formed of two parts 140A and 140B with the second valve 158 located between the two parts.

The second embodiment also includes an air bleed-off valve 174 located at the inlet 133 to the pump 130.

In this embodiment of the irrigation tubing set, preparation and operation is similar to that of the previous embodiment. The irrigation tubing set 110 is connected to the source of fluid 120 which is suspended on an IV pole 162. The tubing set 110 is preferably primed by actuating the pump 130 repeatedly to expel substantially all air from the tubing set. The bleed-off valve 174 may be opened at this stage to assist in expelling air from the tubing set.

The irrigation tubing set 110 is connected to the intraoperative instrument 150 and the clamp 160 is opened. The delivered fluid pressure is provided by the height of the water bag 120 above the intraoperative instrument 150. Like the previous embodiment, the irrigation tubing set 110 has the advantage that it can be used to provide a bolus of water, if desired. In the embodiment of FIG. 2, the physician manually squeezes the bulb pump 130 to deliver a bolus of water to the surgical site. The first valve 135 prevents fluid from flowing from the pump 130 back into the fluid source 120 when the pump 130 is squeezed. The second valve 158 allows fluid to flow from the pump 130 toward the intraoperative instrument, but prevents fluid from being back pressured toward the fluid source 120. Thus, when the physician squeezes the bulb pump 130, the water is forced to flow to the intraoperative instrument 150.

Figure 3:
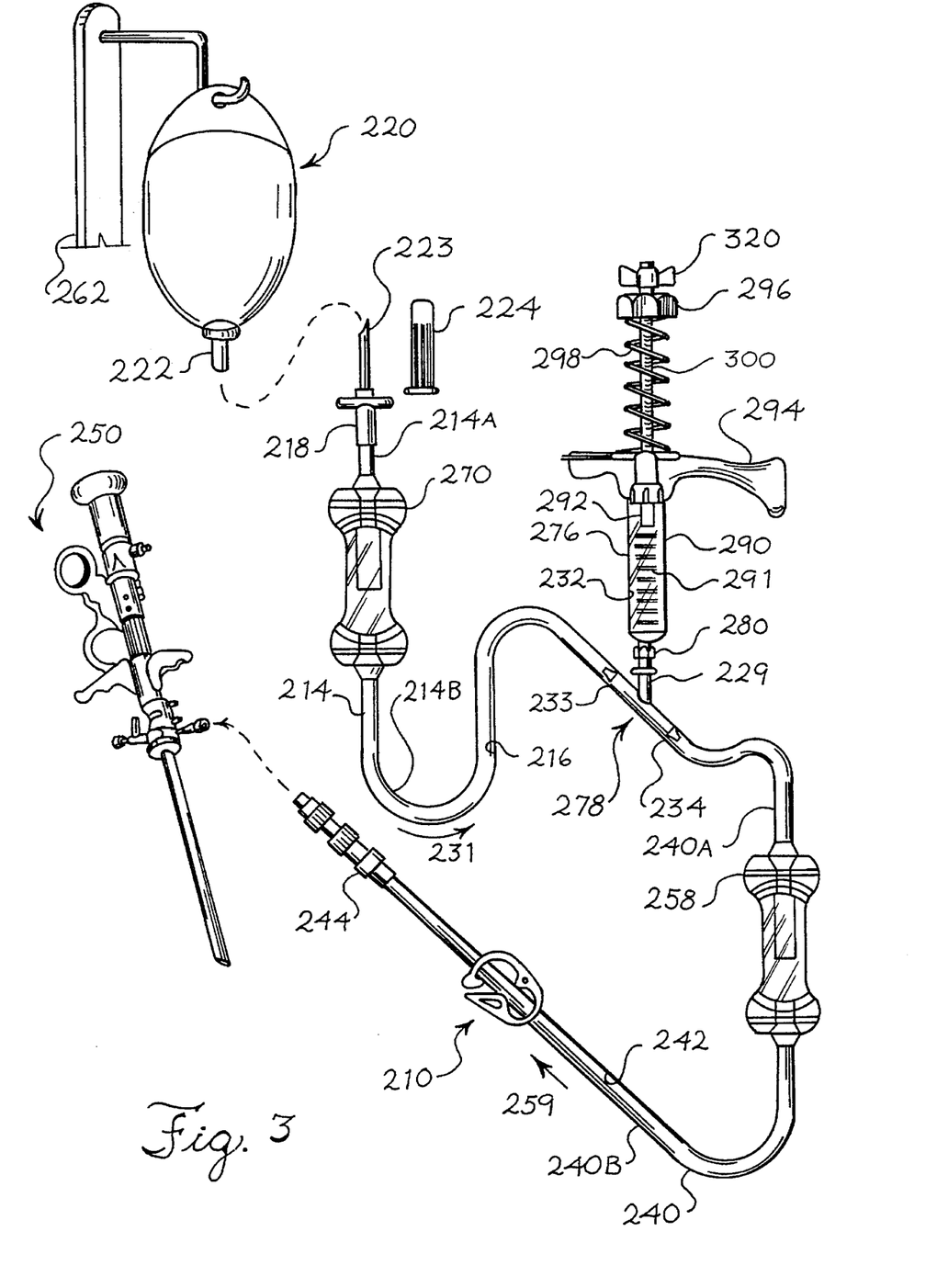
FIG. 3 is a perspective view similar to that of FIG. 1 showing still another embodiment of the present invention.
Figures 4, 5:
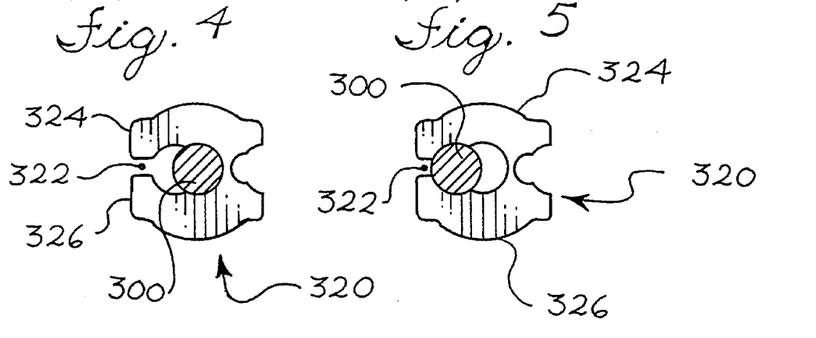
FIG. 4 is a top view of portions of the adjusting nut and rod shown in the embodiment of FIG. 3.
FIG. 5 is a top view similar to FIG. 4 of the portions of the adjusting nut and rod shown in another position.

Referring to FIGS. 3–5, there is shown a third embodiment of the present invention. The third embodiment is similar in certain respects to the first and second embodiments, and similar components are indicated by the same numerals incremented by 200 relative to FIG. 1. Components in the third embodiment may have the same size and composition as similar components in the first and second embodiments.

Referring to FIG. 3, an irrigation tubing set 210 has a first section of tubing 214 that defines a first fluid passage 216. A fitting 218, such as a spike 223, provides for a suitable connection with a fitting 222 on a source of irrigating fluid 220. A spike cover 224 is provided.

Connected to the first section of tubing 214 is a pump 230. In this embodiment, the pump 230 includes a syringe 276. The syringe 276 is connected to the first section of tubing 214 by means of a Y-connector 278. The Y-connector 278 has an inlet 233, an outlet 234, and a syringe port 229. The syringe 276 has a nozzle 280 that connects to the syringe port 229 of the Y-connector 278.

The syringe 276 has a hollow cylindrical barrel or body 290 defining an internal volume 232 of approximately 10 cc. The barrel 290 is preferably made of a transparent plastic and is marked with observable graduations 291 along its length to indicate the internal volume. The nozzle 280 communicates with the internal volume 232 inside the barrel 290. A plunger 292 is slidably movable inside the barrel 290 opposite the nozzle 280. A handle grip 294 is fixedly mounted on the outside of the barrel 290. An actuator button 296 is located on an outside end of the plunger 292. The actuator button 296 is sized relative to the handle grip 294 so that a person can manually grasp the handle grip 294 with his fingers while operating the actuator button 296 with his thumb. A spring 298 is mounted between the actuator button 296 and the barrel 290 to bias the actuator button 296 and attached plunger 292 toward a retracted (outward) position relative to the barrel 290. A threaded rod 300 is fixedly connected at one end to the handle grip 294. The actuator button 296 includes a slotted opening 304 aligned with the rod 300 and through which part of the threaded rod 300 is received.

An adjusting nut 320 is positioned on the threaded rod 300 so that the slotted opening 304 of the actuator button 296 is between the adjusting nut 320 and the handle grip 294. As best seen in FIGS. 4 and 5, the adjusting nut 320 is formed of a resilient U-shaped clip. The adjusting nut 320 has a slot 322 therethrough formed by resilient sides 324 and 326. The shape of the slot 322 provides for two positions of different dimensions. When the threaded rod 300 is in the slot 322 of the adjusting nut 320 in the position shown in FIG. 4, the sides 324 and 326 tightly engage the threaded rod 300 so that the adjusting nut 320 cannot be slid longitudinally along the threaded rod 300. However, although the adjusting nut 320 cannot slide along the threaded rod 300 when it is in the engaged position shown in FIG. 4, it can be rotated relative to the threaded rod 300. The sides 324 and 326 of the adjusting nut 320 have internal threads that are matable with the threads on the threaded rod 300 so that when the adjusting nut 320 is in the position of FIG. 4, the adjusting nut 320 can be advanced and retracted along the threaded rod 300 by rotation of the adjusting nut 320 on the threaded rod 300. When the threaded rod 300 is in the slot 322 of the adjusting nut 320 in the position of FIG. 5, the sides 324 and 326 do not tightly engage the threaded rod 300 and the adjusting nut 320 can be slid along the rod 300 without rotation.

The parts of the pump 230 are preferably made of a suitable plastic, except for the spring 298 which is made of a suitable metal. The syringe 276 may be commercially available syringe, such as the pump syringe available from Braun, of Bethelmem, Pa.

Connected to an outlet 234 of the Y-connector 284 is a second section of tubing 240 defining a second fluid passage 242. Located at a distal end of the second section of tubing 240 is a second fitting 244 that provides for a suitable connection with a fitting 252 on an intraoperative instrument 250. A tubing clamp 260 is located on the second section of tubing 240.

Like the other embodiments, the third embodiment includes a first valve 235 located in the first fluid passage 216 to restrict flow to the direction of arrow 231. The first tubing section 214 is formed of two parts, 214A and 214B, with the first valve 235 located between the two parts.

A second valve 258 is located in the second fluid flow passage 242 to restrict flow in the direction 259 from the pump 230 toward the intraoperative instrument 250. The second tubing section 240 is formed of two parts, 240A and 240B, with the second valve 258 located between the two parts.

In the third embodiment of the irrigation tubing set 210, preparation and operation is similar to that of the other two embodiments. The irrigation tubing set 210 is connected to the source of fluid 220 which is suspended on an IV pole 262 and primed by actuating the pump 230.

When the surgical procedure is being conducted in a relatively constrained area of the body or when the patient is relatively small, e.g. an infant, it may be preferable that the bolus of water is restricted to a specific amount. In the embodiment shown in FIGS. 3–5, the volume of the fluid bolus that can be delivered to the patient can be adjusted with precision. This is accomplished by adjusting the syringe pump volume prior to use. To adjust the syringe volume, the front end of the plunger 292 inside the syringe barrel 290 is aligned with the required graduation line 291 on the syringe barrel 290. The adjusting nut 320 is moved to the disengaged position on the threaded rod 300 (i.e., as shown in FIG. 5). The adjusting nut 320 is slid along the threaded rod 300 until it stops against the actuator button 296. The adjusting nut 320 is shifted on the threaded rod 300 from the disengaged position to the engaged position (i.e., as shown in FIG. 4). The adjusting nut 320 may be rotated to achieve precise plunger alignment with the appropriate graduation 291 on the barrel. With the adjusting nut 320 in the engaged position, the plunger 292, biased by the spring 298, can only retract the selected amount thereby precisely establishing the volume of the bolus that is delivered when the physician operates the pump 230 by pressing the actuator button 296.

Once the volume of the syringe 276 is adjusted, the irrigation tubing set 210 can be operated in a manner similar to the previously described embodiments. The irrigation set 210 is connected to the intraoperative instrument 250 and the clamp 260 is opened. In the embodiment of FIGS. 3–5, the physician manually squeezes the syringe pump to deliver a bolus of water to the surgical site. If the physician desires to adjust the volume of the water bolus during an intraoperative procedure, the volume can be adjusted at any time by following the steps set forth above.

Figure 6:
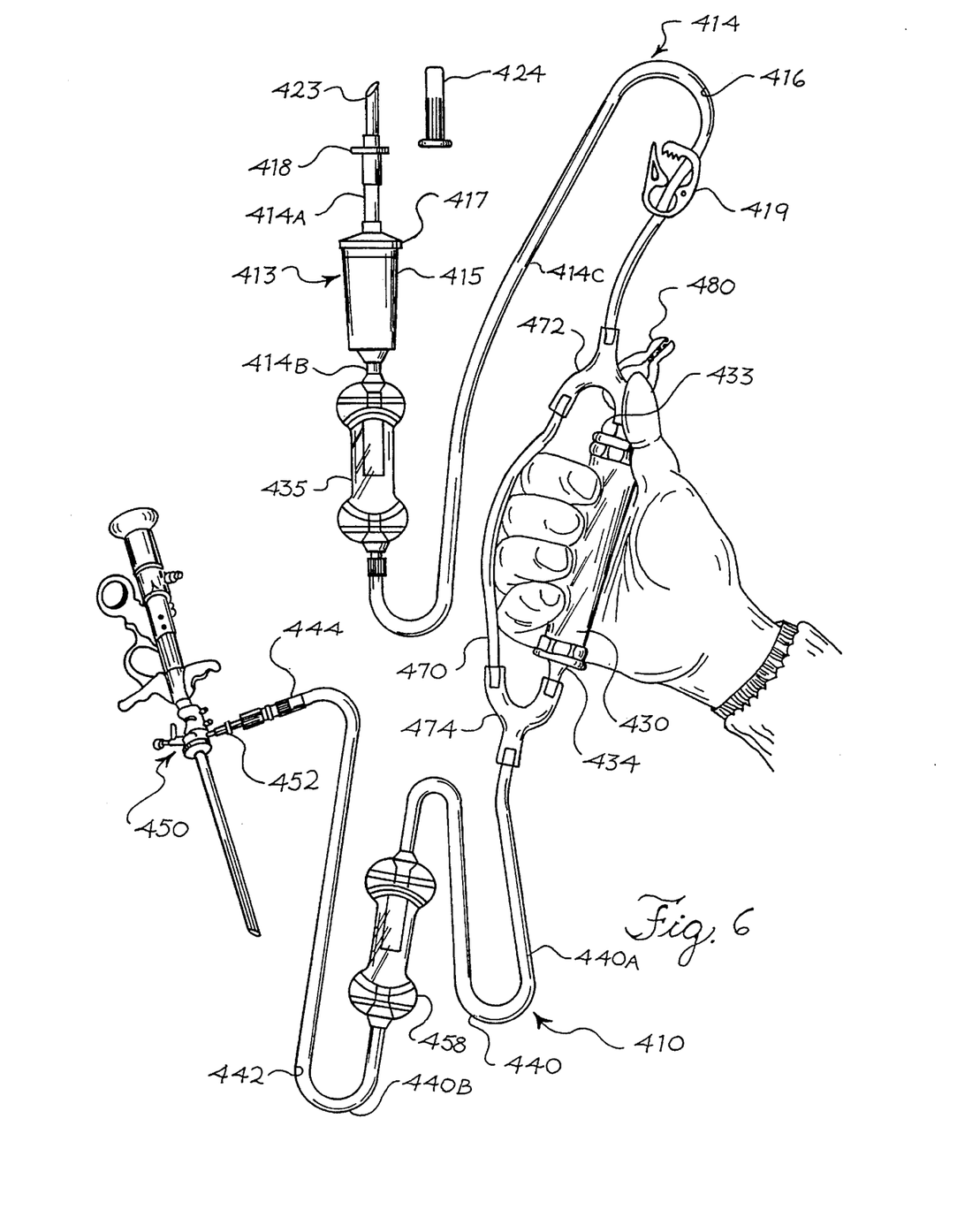
FIG. 6 is a perspective view similar to that of FIG. 1 showing still another embodiment of the present invention.

Referring to FIG. 6, there is shown a fourth embodiment of the present invention. The fourth embodiment is similar to the previous embodiments and similar components are indicated by the same numerals incremented by 400 relative to the first embodiment. Components in the fourth embodiment may have the same size and composition as similar components in the previous embodiments, except as noted.

In FIG. 6, there is an irrigation tubing set 410 having a first section of tubing 414 that defines a first fluid passage 416. The first tubing section 414 is formed of three parts, 414A, 414B, and 414C with a first valve 435 located between the parts 414B and 414C. A fitting 418, such as a spike-type fitting 423, provides for a suitable connection with a fitting 422 on a source of irrigating fluid (not shown). A spike cover 424 is provided.

In the embodiment of FIG. 6, the fitting 418 connects to a first part 414A of the first tubing section 414. A flow chamber 413 is connected between the first part 414A and the second part 414B of the first tubing section 414. The flow chamber 413 includes a hollow transparent plastic cylindrical body 415 and a cap 417. Fluid from the source 420 is received in the flow chamber 413 and maintains a fluid level therein. The flow chamber 413 typically is located below the fitting 418 when the tubing set 410 is connected to a source of fluid suspended from IV pole. The fluid flow rate may be adjusted by means of a racheted clamp 419 located along the first tubing section 414. The flow rate may be adjusted so that fluid regularly drips into the flow chamber 413 from the source. Thus, by observing the dripping of fluid and the fluid level in the flow chamber 413, the physician can be assured that fluid is flowing through the tubing set 410. The flow chamber 415 and cap 417 may be composed of suitable transparent plastic material such as PVC.

Connected to a distal end of the first section of tubing 414 is a pump 430 which in this embodiment is a tubular pump as in the first embodiment. Connected to an outlet 434 of the pump 430 is a second section of tubing 440 defining a second fluid passage 442. Located at a distal end of the second section of tubing 440 is a second fitting 444 that provides for a suitable connection with a fitting 452 on an intraoperative instrument 450. A valve 458 is located in the second fluid flow passage 442 to restrict flow in the direction from the pump 430 toward the intraoperative instrument 450. The first and second valves 435 and 458 may be a pillow-type valves as in the second embodiment described above.

Connected across the pump 430 is a third section 470 of tubing. The third tubing section 470 connects to the first tubing section 414 at the inlet 433 of the pump 430. Connection between the first tubing section 414, the third tubing section 470, and the pump 430 is made by means of a first soft horseshoe Y-fitting 472. The third tubing section 470 also connects to the second tubing section 440, and specifically to the first part 440A of the second tubing section 440, at an outlet 434 of the pump 430. The second tubing section 440, the third tubing section 470, and the outlet 434 of the pump 430 are connected by means of a second soft horseshoe Y-fitting 474. The third section 470 of tubing is spaced away from the tubular pump 430 so that the physician can place his fingers between the pump 430 and the third section of tubing 470. This provides for a convenient hand grip feature so that the physician can squeeze and let go of pump 430 without having the pump 430 slip away from him. In addition, the third section of tubing 470 also helps to enhance the flow rate through the irrigation set 410.

In this embodiment, the first and second sections of tubing 414 and 440 are formed of PVC tubing with an I.D. of 0.2 inch and an O.D. of 0.28 inches. The first part 414A of the first section of tubing is approximately 2 inches in length, the second part 414B is approximately 0.5 inches in length, and the third part 414C is approximately 96 inches in length. The first part 440A and the second part 440B of the second section of tubing are each approximately 12 inches in length.

This embodiment also includes a sheet clip 480. The function of the sheet clip 480 is to allow for convenient attachment of the tubing set 410 to a patient drape so that the tubing set can be kept close at hand after the physician releases the tubing set to perform other tasks.

Figure 7:
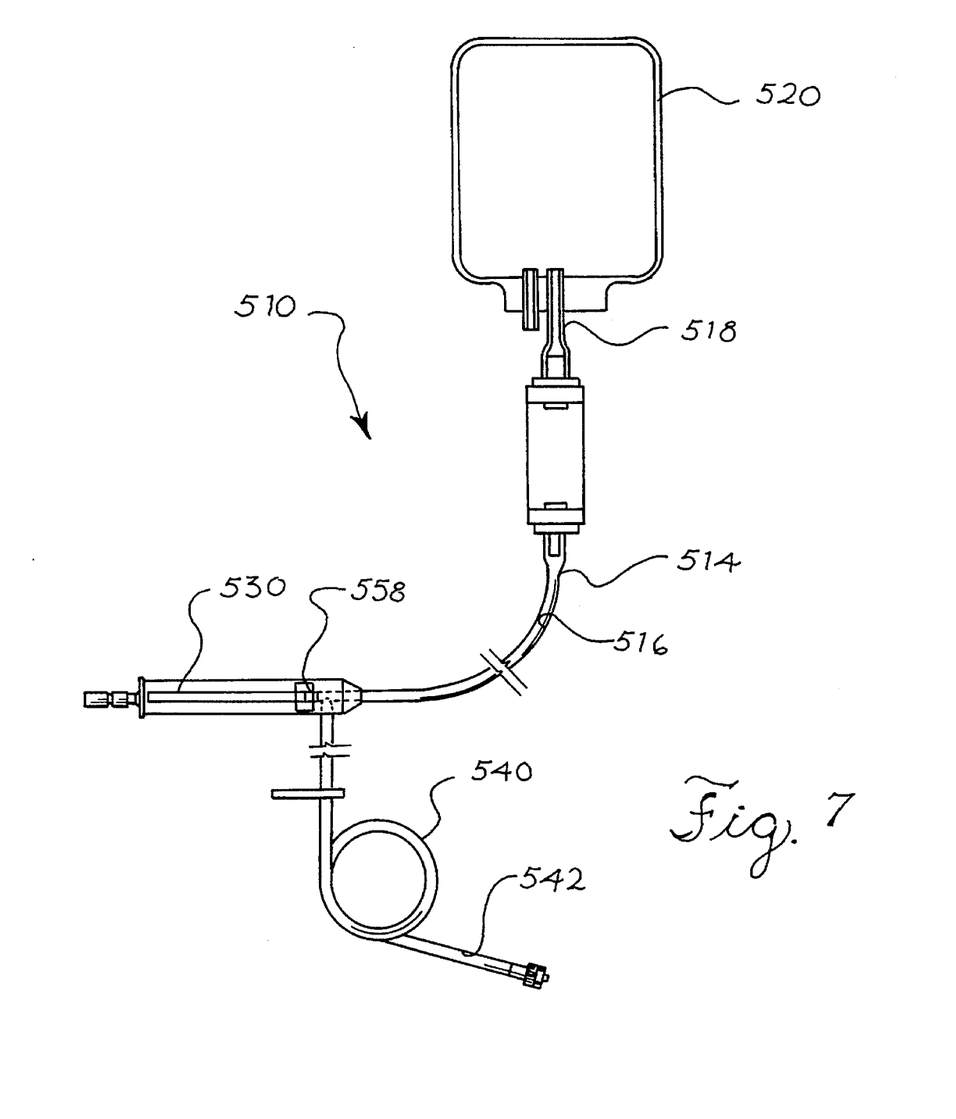
FIG. 7 is a perspective view similar to that of FIG. 1 showing yet another embodiment of the present invention.

Referring to FIG. 7, there is shown a fifth embodiment of the present invention. The fifth embodiment is similar to the previous embodiments and similar components are indicated by the same numerals incremented by 400.

In the embodiment of FIG. 7, there is an irrigation tubing set 510 having a first section of tubing 514 defining a first fluid passage 516 and having a fitting 518 for making a connection with a source of irrigating fluid 520. Connected to the opposite end of the first section of tubing 514 is a pump 530 which in this embodiment is a tube pump. As in the previous embodiments, a second section of tubing 540 defines a second fluid passage 542 and connects the pump 530 to an intraoperative instrument (not shown).

In this embodiment, the function of the first and second valves is provided by a combination-shuttle valve 558. The combination shuttle-type valve 558 restricts flow in the first and second fluid flow passages 514 and 540 in a direction from the source 520 toward the intraoperative instrument. The combination shuttle valve 538 is commercially available from American Manufacturing and Technologies, Inc., of Addison, Ill. The combination shuttle valve 538 connects the pump 530 and the first and second sections of tubing 514 ill and 540.

It is intended that the foregoing detailed description be regarded as illustrative rather than limiting and that it is understood that the following claims including all equivalents are intended to define the scope of the invention.

We claim:

1. A tubing set for use with a source of irrigating fluid and an intraoperative medical instrument having a fluid passage inlet, comprising:

a first fluid passage section communicating with an inlet for connection to the source of fluid;

a second fluid passage section communicating with an outlet for connection to the intraoperative medical instrument;

a pump for delivering a bolus of fluid, said pump connected between said first fluid passage section and said second fluid passage section; and a first valve located between said inlet and said outlet to the medical instrument to prevent flow in a direction toward said inlet, but permit flow in a direction toward said outlet.

2. The invention of claim 1 wherein said first fluid passage section, said pump, and said second fluid passage section define a flow path that provides a continuous trickle of fluid from the source of irrigating fluid to the intraoperative medical instrument.

3. The invention of claim 1 in which said first valve is located between said inlet for connection to said source of fluid and said pump, and further in which the invention further comprises:

a second valve located between said pump and said outlet to the medical instrument,.

4. The invention of claim 3 in which said second valve is oriented to restrict flow of fluid in said second fluid passage section to a direction from said pump to said intraoperative instrument.

5. The invention of claim 1 further comprising:

a clamp located along the second fluid passage section, said clamp having a closed position wherein flow through said second section is prevented, an open position wherein said clamp does not impede flow through said second section, and at least one additional position wherein flow through said second section is partially impeded.

6. The invention of claim 1 in which said pump is manually operable.

7. The invention of claim 1 in which said pump is a bulb pump.

8. The invention of claim 1 in which said pump is a tubular pump.

9. The invention of claim 1 in which said valve is a pillow type valve.

10. The invention of claim 1 in which said valve is a check valve.

11. The invention of claim 1 wherein said pump has a volume of approximately 10 cubic centimeters.

12. The invention of claim 1 in which said pump includes observable graduations indicating volumes within said pump.

13. The invention of claim 1 further comprising:

a bleed off valve located at said pump to facilitate removing air from tubing set.

14. The invention of claim 1 further comprising:

a mechanism associated with said pump to regulate an amount of said bolus.

15. The invention of claim 14 wherein said mechanism comprises:

a threaded rod connected to said pump; and an adjusting nut positionable along said threaded rod to define a maximum intake into said pump.

16. The invention of claim 1 in which said pump is a syringe.

17. The invention of claim 16 further comprising:

a tubing connector having three ports, said tubing connecter connected to a nozzle of said syringe, said first fluid passage section, and said second fluid passage section.

18. The invention of claim 1 in which said pump fills with fluid and assumes an expanded size under pressure applied by the source of fluid.

19. The invention of claim 1 wherein said first valve is prevents flow of fluid through said first fluid passage section in a direction from said pump to said inlet from said source of fluid.

20. The invention of claim 1 further comprising:

a hand grip located along side of said pump.

21. The invention of claim 1 further comprising:

a drip chamber located between said inlet and said outlet to the medical instrument.

22. A tubing set for connecting a source of fluid to an intraoperative medical instrument having a fluid passage, comprising:

a first fluid passage section having an inlet for connection to the source of fluid;

a second fluid passage section having an outlet for connection to the medical instrument;

a pump connected between said first fluid passage section and said second fluid passage section;

a first valve located between said pump and the intraoperative medical instrument for restricting flow in said second fluid passage section to a direction from said pump to the medical instrument; and a second valve located between said pump and the source of fluid for restricting flow in said first fluid passage section to a direction from the source of fluid to said pump.

23. The invention of claim 22 wherein said first fluid passage section, said pump, and said second fluid passage section define a flow path that provides a continuous, gravity-fed trickle of fluid from the source of irrigating fluid to the intraoperative medical instrument.

24. A method for providing a fluid to a surgical site comprising the steps of:

attaching an outlet of a fluid source to an inlet of a tubing set;

attaching an outlet of the tubing set to an inlet of a surgical instrument;

permitting a trickle of irrigating fluid to flow from the fluid source through the tubing set to the surgical instrument; and operating a pump connected between a first portion of the tubing set and a second portion of the tubing set to deliver a bolus of fluid to the surgical instrument.

25. The method of claim 24 wherein said step of permitting a trickle of irrigating fluid further comprises the step of:

suspending the fluid source at an elevation above the surgical instrument so as to deliver a trickle of irrigating fluid through the tubing set from the source of irrigating fluid to the surgical instrument.

26. The method of claim 24 further comprising the step of:

adjusting a clamp located along said tubing set to restrict the flow therethrough.

27. The method of claim 24 wherein said step of operating a pump is performed manually.

28. The method of claim 27 wherein said step of manually operating a pump comprises the step of squeezing a bulb pump.

29. The method of claim 27 wherein said step of manually operating a pump comprises the step of operating a syringe.

30. The method of claim 24 further comprising the step of:

priming the irrigation tubing set to remove air from therewithin.

31. The method of claim 30 wherein the priming step further comprises:

operating a bleed off valve located on the irrigation tubing set to remove air from therewithin.

* * * * *